United States Patent [19]

Ogawa et al.

[11] 4,103,083

[45] Jul. 25, 1978

[54] NOVEL ANTIBIOTICS DERIVATIVES AND PROCESS FOR PREPARING THE SAME

[75] Inventors: Yasuaki Ogawa; Yasumitsu Kondo; Takashi Shomura, all of Yokohama; Takashi Tsuruoka, Kawasaki; Shigeharu Inouye, Yokohama; Taro Niida, Yokohama, all of Japan

[73] Assignee: Meiji Seika Kaisha, Ltd., Tokyo, Japan

[21] Appl. No.: 751,877

[22] Filed: Dec. 17, 1976

Related U.S. Application Data

[63] Continuation of Ser. No. 553,710, Feb. 27, 1975, abandoned.

[51] Int. Cl.$^2$ ............................................. C07D 501/20
[52] U.S. Cl. ...................................... 542/427; 544/20; 544/21; 195/80 R; 424/246
[58] Field of Search .......................... 260/240 J, 243 E; 542/427; 544/20, 21, 30, 34

[56] References Cited

U.S. PATENT DOCUMENTS

| | | | |
|---|---|---|---|
| 2,505,374 | 4/1950 | Wirtel et al. | 260/705 X |
| 3,297,692 | 1/1967 | Flynn | 260/243 C |
| 3,351,597 | 11/1967 | Higgens | 260/243 C |
| 3,452,096 | 6/1969 | Paleveda, Jr. et al. | 260/705 X |
| 3,718,644 | 2/1973 | Weston et al. | 260/240 J |
| 3,852,277 | 12/1974 | Jacobus et al. | 260/240 J |
| 3,914,157 | 10/1975 | Stapley et al. | 260/243 C X |
| 4,007,178 | 2/1977 | Berges | 260/243 C |

*Primary Examiner*—Arthur P. Demers
*Attorney, Agent, or Firm*—Sughrue, Rothwell, Mion, Zinn and Macpeak

[57] ABSTRACT

Novel antibiotics derivatives 7-(5-acylamido-5-carboxyvaleramido)-3-(α-methoxy-p-acyloxycinnamoyloxymethyl)-7-methoxy-3-cephem-4-carboxylic acids and the salts thereof which are useful as antibiotics and intermediates for the preparation of cephamycin derivatives, a process for preparing the same, and a process for recovering the cephamycin derivatives effectively and stably from the fermentation broth in the form of an N-acyl derivative.

3 Claims, No Drawings

NOVEL ANTIBIOTICS DERIVATIVES AND PROCESS FOR PREPARING THE SAME

This is a Continuation, of application Ser. No. 553,710, filed Feb. 27, 1975, now abandoned.

BACKGROUND OF THE INVENTION

1. Field of the Invention

This invention relates to novel cephemycin derivatives and a process for preparing the same. More particularly, this invention relates to 7-(5-acylamido-5-carboxyvaleramido)-3-(α-methoxy-p-acyloxycinnamoyloxymethyl)-7-methoxy-3-cephem-4-carboxylic acids represented by the formula (I)

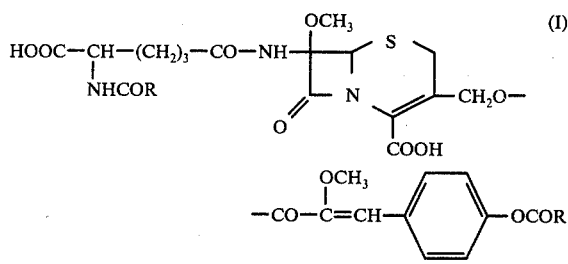

wherein R represents an alkyl group having 1 to 4 carbon atoms which may be substituted with halogen atoms; an aryl group; an arylalkyl group having 1 to 4 carbon atoms in the alkyl moiety; an alkoxy group having 1 to 4 carbon atoms which may be substituted with halogen atoms; or an arylalkoxy group having 1 to 4 carbon atoms in the alkoxy moiety; the aryl moiety of the aryl, arylalkyl or arylalkoxy group being optionally substituted with halogen atoms, and the salts thereof, and a process for preparing the compounds of the formula (I).

2. Description of the Prior Art 7-(5-carboxyvaleramido)-3-(α-methoxy-p-hydroxycinnomoyloxymethyl)-7-methoxy-3-cephem-4-carboxylic acid of the formula (II) hereinafter given has been isolated as a fermentation product of some kinds of Streptomyces by Stapley as disclosed in Japanese Patent Application OPI Nos. 3286/1971 and 1876/1972. However, as is described in the reports of *Antimicrobial Agents and Chemotherapy* 2, 132–135, 1972, it is very difficult to obtain the compound of the formula (II) in a highly purified state since the compound is relatively unstable and the yield of the compound has been reported to be very low, i.e., about 10 to 15% at best.

As a result of various investigations on a method for easily isolating the compound of the formula (II) from the fermentation broth or a filtrate obtained from the fermentation broth, it was found that the compound of the formula (II) can be isolated effectively and stably by a solvent extraction method in the form of novel acyl derivatives having the formula (I) while retaining the antimicrobial activity of the parent compound of the formula (II) and that the N-acyl derivatives so obtained can be used as raw material for the synthesis of various antimicrobial agents, for example, Cefoxitin as hereinafter described in greater detail.

SUMMARY OF THE INVENTION

A primary object of this invention is therefore to provide novel cephamycin derivatives, 7-(5-acylamido-5-carboxyvaleramido)-3-(α-methoxy-p-acyloxycinnamoylmethyl)-7-methoxy-3-celphem-4-carboxyic acids represented by the formula (I).

Another object of the present invention is to provide a process for preparing the novel cephamycin derivatives of the formula (I).

A further object of the present invention is to provide a process for effectively isolating 7-(5-amino-5-carboxyvaleramido) -3-(α-methoxy-p-hydroxycinnamoyloxymethyl)-7-methoxy-3-cephem-4-carboxylic acid of the formula (II) in the form of an acyl derivative thereof from the fermentation broth by a solvent extraction.

DETAILED DESCRIPTION OF THE INVENTION

The cephamycin derivatives of the present invention, i.e., 7-(5-acylamido-5-carboxyvaleramido)-3-(α-methoxy-p-acyloxy-cinnamoyloxymethyl)-7-methoxy-3-cephem-4-carboxylic acids of the formula (I) above can be prepared by reacting 7-(5-amino-5-carboxyvaleramido)-3-(α-methoxy-p-hydroxycinnamoyloxymethyl)-b 7-methoxy-3-cephem-4-carboxylic acid of the formula (II)

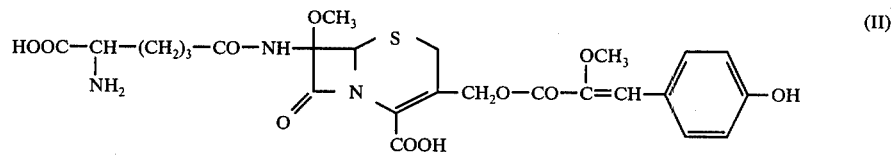

with an acylating agent of the formula (III)

RCOX (III)

wherein R is as defined above and X represents a halogen atom.

The term "lower alkyl group" used throughout the specification and claims of the present invention designates a straight or branched chain alkyl group having 1 to 4 carbon atoms, which may be substituted or unsubstituted with halogen atoms, for example, a methyl, ethyl, n-propyl, iso-propyl, n-butyl, secbutyl, t-butyl, trichloromethyl group and a like group.

The term "lower alkoxy group" designates a straight or branched alkoxy group having 1 to 4 carbon atoms, which may be substituted or unsubstituted with halogen atoms, for example, a methoxy, ethoxy, butoxy, trichloropropoxy group and a like group.

The term "aryl group" designates a phenyl group, a halogen substituted phenyl group, a benzyl group, a pyridyl group, a thienyl group and the like.

The term "halogen" designates a chlorine, bromine or iodine atom, preferably a chlorine or bromine atom.

The starting material, 7-(5-amino-5-carboxyvaleramido)-3-(α-methoxy-p-hydroxycinnamoyloxymethyl)-7-methoxy-3-cephem-4-carboxylic acid of the formula (II) above can easily be obtained as a fermentation product by cultivation of *Streptomyces griseus* as disclosed in Japanese Patent Application OPI No. 1876/1972 or by cultivation of *Streptomyces viridochromogenes* SF-1584 strain isolated by the present inventors. The specimen of *Streptomyces viridochromogenes* SF-1584 has been deposited at the Fermentation Research Institute, Agency of Industrial Science & Technology, Japan, under the deposit No. 2288, deposited on Sept. 27, 1973.

The microbiological characteristics of *Streptomyces viridochromogenes* SF-1584 strain are as follows:

(I) Morphological Characteristics:

Aerial mycelium grows well on a starch agar medium, a yeast malt agar medium and an oatmeal agar medium, etc. The formation of spores is abundant. Monopodial branching is observed but no whorl is observed. The terminal of the serial mycelium is spiral (open spiral). Special structure such as sclerotium is not observed. On electron microscopic observation, the surface of spores is spiny. The shape of spores is oval to ellipsoidal, 0.5 to 0.8 × 0.8 to 1.0 micron is size. The spores are usually arranged in a chain of more than 10 spores.

(II) Growth on Medium (Cultured at 28° C):

| Medium | Growth (Reverse Color) | Aerial Mycelium | Soluble Pigment |
|---|---|---|---|
| Sucrose-Nitrate Agar | Dark Cream to Pale Grayish Yellow | White | None |
| Glucose-Asparagin Agar | Pale Yellowish Brown | Scant, White | None |
| Glycerin-Asparagin Agar | Grayish Yellow | Scant, Pale Yellowish Green | None |
| Starch Agar | Good, Grayish Olive to Yellowish Brown | Abundant, Greenish Blue | None |
| Oatmeal Agar | Good, Grayish Olive (Color changes to slightly reddish color upon addition of 0.05N HCl) | Abundant, Blue to Grayish Green | Pale Green |
| Yeast Malt Agar | Good, Grayish Olive to Brown | Abundant, Grayish Blue | None |
| Nutrient Agar | Poor, Colorless | None | None |
| Tyrosin Agar | Pale Brown to Brown | Abundant, Greenish Blue to Grayish Blue | Pale Brown |

(III) Physiological Characteristics:

(1) Growth Temperature Range: The strain grows at a temperature of from 15° to 40° C on a starch agar medium.

(2) Liquefaction of Gelatin: Gelatin is slightly liquefied after 30 days' cultivation at 20° C.

(3) Hydrolysis of Starch: Positive (at 28° C)

(4) Coagulation of Skim Milk: Negative (at 28° C)
Peptonization of Skim Milk: Positive (at 28° C)

(5) Formation of Melanin-like Pigment: Positive (doubtful) to positive (IV) Utilization of Carbon Sources (estimated in Pridham-Gottlieb Agar Medium)

The stran well utilizes the following carbon sources: D-glucose, D-fructose, D-mannitol, D-xylose, L-arabinose, L-inositol, rhamnose, sucrose and raffinose.

As a result of investigations on the characteristics of SF-1584 strain with reference to the characteristics of wellknown strains according to the criterion given in S. A. Waksman, The Actinomycetes, Vol. 2, 1961; R. Hutter, Systematik der Streptomyceten, 1967; and *International J. Systematic Bacteriology,* Vol. 18, pp69–189, pp279–392, 1968; ibid, Vol. 19, pp391–512, 1969; ibid, Vol. 22, pp265–394, 1972, the SF-1584 strain was identified as a strain of *Streptomyces viridochromogenes.*

The strain of *Streptomyces viridochromogenes* SF-1584 can be cultivated in a conventional manner in a culture medium containing general carbon and nitrogen sources which are assimilable by ordinary microorganisms. The nutrient sources which can be used in the present invention are those well known in the art which are commonly employed in the cultivation of strains of *Streptomyces.*

Suitable examples of the carbon sources are glucose, sucrose, starch, dextrin, glycerin, sugar syrup, soybean oil and the like. Suitable examples of the nitrogen sources are soybean meal, wheat-embryo, meat-extract, peptone, dried yeast, corn steep liquor, ammonium sulfate and the like.

Inorganic salts such as calcium carbonate, sodium chloride, potassium chloride, phosphates and the like can also be used, if desired, in the medium together with other organic and inorganic material which aid the growth of the strain and promote the production of the compound of the formula (II).

The cultivation can be carried out by conventional procedures which are commonly employed in the producton of antibiotics by fermentation. It is, however, advantageous to use a liquid cultivation method, in particular, a liquid cultivation under submerged conditions. The cultivation can suitably be effected under aerobic conditions at a temperature in the range of from about 25° to about 35° C, preferably at about 28° C. The concentration of the desired compound of the formula (II) in the resulting culture generally reaches maximum at the end of 3 to 6 days' cultivation in either the shake-cultivation or tank-cultivation procedure.

The compounds of the present invention represented by the formula (I) above can be prepared by adding the acylating agent represented by the formula (III) to a fermentation broth obtained by culturing *Streptomyces griseus* or *Steptomyces viridochromogenes* SF-1584 strain, the fermentation broth which is partially purified and concentrated or a solution of the isolated pure compound of the formula (II). The solution which is used in the acylation includes water or a mixture of water and an organic solvent such as acetone, dioxane, dimethylformamide, dimethylsulfoxide, pyridine and the like. The concentration of the solution of the compound of the formula (II) in the above medium is not critical, but the concentration is preferably in the range of from about 0.5 to 50 mg/ml.

Representative examples of the acylating agents of the formula (III) which can be used in the present invention are alkoxycarbonyl halides such as carbomethoxy chloride, carboethoxy chloride, carbo-n-butoxy chloride, carbotrichloropropoxy chloride and the like, arylalkoxycarbonyl halides such as carbobenzyloxy chloride and the like, acyl halides such as acetyl chloride, acetyl bromide, propionyl chloride, butyryl chloride, pivaroyl chloride, trichloroacetyl chloride and the like, and arylacyl halides such as isonicotinyl chloride, phenylacetyl chloride, phenoxyacetyl chloride and the like, and aroyl halides such as benzoyl chloride, p-chlorobenzoyl chloride and the like. The acylating agent is generally used in an amount of 2 to 40 moles, preferably 4 to 20 moles, based on the amount of the compound of the formula (II).

The acylation reaction can be carried out at a temperature between a cooling temperature to about 50° C, but is advantageously effected at or below room temperature (about 20°–30° C) since the starting material of the formula (II) and the product of the formula (I) are relatively unstable at high temperatures. The reaction time generally varies depending upon the temperature, the pH of the acylation reaction system and the amount of reagents used, but usually from about 3 to about 15 hours. The acylation is usually effected at a pH of about 7 to about 9, preferably at a pH of 7.5 to 8. In order to maintain the reaction mixture within the above pH range, a basic material such as an alkali metal hydroxide, for example, sodium hydroxide, potassium hydroxide and the like, an alkali metal carbonate or bicarbonate, for example, sodium carbonate, sodium bicarbonate and the like, a tertiary amine, for example, triethylamine, pyridine and the like or a mixture of various bases described above can be added to the reaction mixture during the acylation reaction for neutralizing the hydrogen halide formed by the acylation reaction.

The isolation of the product of the formula (I) can be effected by taking advantage of a higher oil-solubility of the product than that of the starting material of the formula (II). For example, when the reaction mixture contains organic solvents, the solvent is removed as completely as possible by, for example, evaporation, from the reaction mixture, and the remaining aqueous reaction mixture is rendered acidic pH followed by extraction with a solvent which is immiscible with water, such as ethyl acetate, butyl acetate, chloroform and the like to extract the desired product into the organic solvent. Alternatively, the product precipitates from the reaction mixture, depending upon the type of the acyl group in the product, for example, ethoxycarbonyl group, and thus can be isolated using a precipitation technique in combination with filtration, decantation, etc.

The product thus obtained is a dibasic acid which is capable of forming a water-soluble metal salt or an organic amine salt, and can be purified advantageously utilizing this property. For example, the product can be purified by extracting the above organic solvent extract or an organic solvent solution of the above precipitate with an aqueous alkaline solution and then back extracting the resulting aqueous alkaline solution under acidic condition with a solvent which is immiscible with water. Also, other purification procedures which are generally used for the purification of organic compounds, such as a counter-current distribution, a column chromatography, etc. can be used for the purification of the product of the formula (I).

The compounds of the formula (I) thus obtained is novel compounds, not previously disclosed in literature. They are sparingly soluble in water and petroleum ether, but soluble in organic solvents such as methanol, ethanol, butanol, acetone, ethyl acetate, butyl acetate, chloroform, etc. or an aqueous solution of an alkali. The products having an alkoxy or arylalkoxy group as an acyl group possess an oil-soluble property higher than that of the products containing an alkyl or arylalkyl group as an acyl group.

As described previously, the compounds of the formula (I) above can form a water-soluble alkali metal salt such as a sodium, potassium, lithium salt or an organic amine salt such as a triethylamine or piperidine salt. The present invention is contemplated to include both the free carboxylic acid forms as well as the salts thereof.

The compounds of the formula (I) of the present invention exhibit per se an antimicrobial activity on *Staphylococcus aureus* 209P, *Bacillus subtilis, Sarcina lutea, Bacillus stearothermophylis* and the like and, therefore, useful as an antibiotic. For example, the di-O,N-ethoxycarbonyl compound of the formula (I) i.e., 7-(5-ethoxycarboamido-5-carboxyvaleramide)-3-($\alpha$-methoxy-p-ethoxycarbonyloxycinnamoyloxymethyl)-7-methoxy-3-cephem-4-carboxylic acid, showed the following antibacterial activities. These antibacterial activities were determined by dipping a paper disc (18 mm in diameter) in a methanolic solution of the above free acid having a concentration of 1,000 $\gamma$/ml followed by drying, placing the dried paper disc on an agar medium containing each of the test organisms listed below and incubating the medium overnight at a temperature of 37° C.

Table 1

| Test Organisms | Inhibition Zone (mm in diameter) |
| --- | --- |
| *Bacillus subtilis* | 11.2 |
| *Sarcina lutea* | 12.0 |
| *Staphylococcus aureus* 209P | 10.9 |
| *Micrococcus lysodeikticus* 8049 | 25.5 |
| *Bacillus stearothermophilus* | 23.8 |
| *Escherichia coli* | 0 |

Also, the compounds of the formula (I) are useful as a starting material for the preparation of other cephamycin derivatives. For example, the compound of the formula (I) can be converted into a cephamycin derivative, Cefoxitin, the activities of which are described in *British Medical Journal, Vol.* 4, No. 5893, pp653–655, by the following reaction scheme:

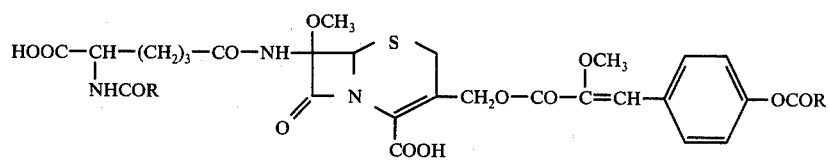

-continued
[Compound of Formula (I)]
↓ Enzymatic Reaction by Esterase or Action of Microorganisms
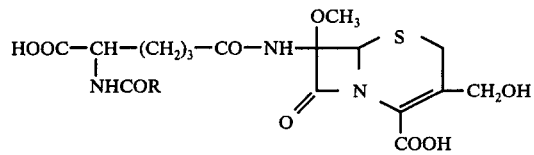
↓ Diphenyldiazomethane/Dioxane at 0° C for 3 hours
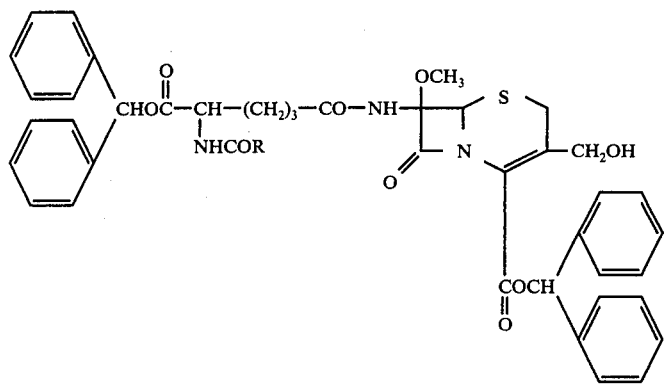
↓ CH₂Cl₂, Collidine and Carbamoyl Chloride, at 0° C for 1 hour
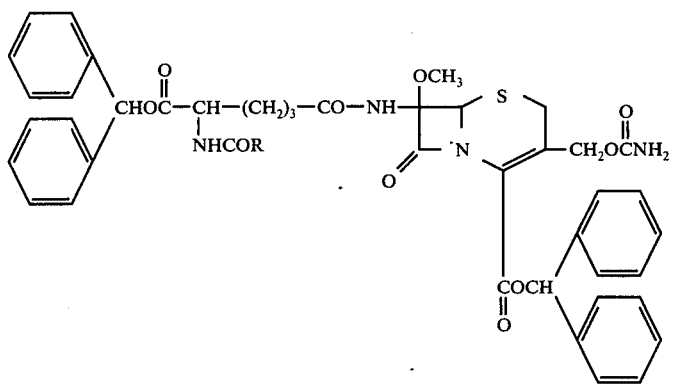
↓ 1) [thiophene]—CH₂CCl (=O)
  N-trimethylsilyltrifluoro-
  acetamide/CH₂Cl₂, at 40° C for 16 hours
2) Zn and Acetic Acid
  (J. Am. Chem. Soc., 1972, No. 164, ORGN 69)

-continued

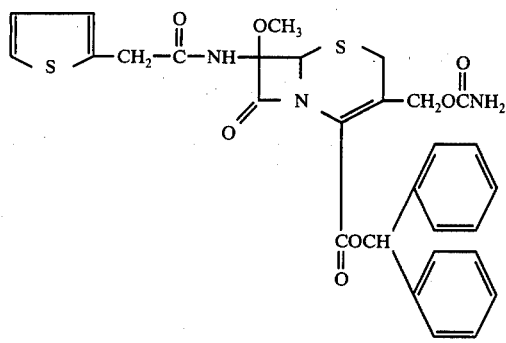

Trifluoroacetic Acid and Anisole,
at 0° C
(J. Am. Chem. Soc., 1972, No. 164,
ORGN 69)

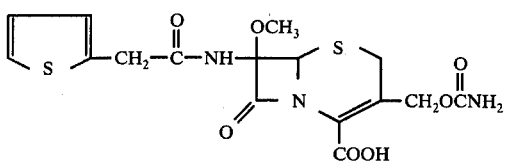

The present invention is further illustrated by the following Examples, but these Examples are given for illustrative purposes only and are not to be construed as limiting the scope of this invention. Unless otherwise indicated, all parts, percents, ratios and the like are by weight.

EXAMPLE 1

0.9 g of 7-(amino-5-carboxyvaleramido)-3-(α-methoxy-p-hydroxycinnamoyloxymethyl)-7-methoxy-3-cephem-4-carboxylic acid was dissolved in 400 ml of water (pH 4.0), and the resulting solution was extracted with two 200 ml portions of ethyl acetate. 30 ml of acetone was added to the aqueous layer of the mixture, and the aqueous layer was then adjusted to a pH of 7.5 with 0.5N sodium hydroxide. A solution of 10 ml of ethoxycarbonyl chloride dissolved in 30 ml of acetone was added dropwise to the mixture while maintaining the reaction mixture at a pH of 7.5 to 8.0 by addition of 0.5N sodium hydroxide. After completion of addition, the reaction mixture was stirred for 1.5 hours at room temperature and adjusted to a pH of 7 with 1N hydrochloric acid. The precipitate formed was isolated by filtration and dissolved in 200 ml of ethyl acetate. The resulting solution was dried over anhydrous sodium sulfate and evaporated to dryness to obtain 1.0 g of 7-(5-ethoxycarboamido-5-carboxyvaleramido)-3-(α-methoxy-p-ethoxycarbonyloxycinnamoyloxymethyl)-7-methoxy-3-cephem-4-carboxylic acid.

The filtrate obtained after isolation of the above precipitate was adjusted to a pH of 2 to 3 with 1N hydrochloric acid and extracted with 300 ml of ethyl acetate. The extract was then back extracted with a 2% aqueous sodium bicarbonate solution and the resulting extract was adjusted to a pH of 2 to 3 with 5N hydrochloric acid. The extract thus obtained was extracted again with 200 ml of ethyl acetate and the ethyl acetate extract was dried and evaporated to dryness to obtain an additional 150 mg of the above product.

Melting Point: 126°–128° C (with decomposition)

Elemental Analysis:
Calcd. for $C_{31}H_{37}N_3O_{15}S$ (%): C, 51.45; H, 5.1; N, 5.8; S, 4.4. Found (%): C, 50.1; H, 5.5; N, 5.3; S, 3.9.

EXAMPLE 2

The microorganism, *Streptomyces viridochromogenes* SF-1584 strain was aerobically cultured in a culture medium containing 1.5% glycerin, 1.5% dextrin, 2.0% soybean meal and 0.15% calcium carbonate at a temperature of 28° C for 65 hours. 4.5 l of the filtrate obtained by filtration of the resulting culture broth to remove mycelium was washed twice with 200 ml of ethyl acetate and 300 ml of acetone was added to the filtrate. A solution of 300 ml of ethoxycarbonyl chloride dissolved in 500 ml of acetone was then added dropwise to the mixture while maintaining the mixture at a pH of 7.5 to 8.0 by addition of 5N sodium hydroxide. After completion of the addition, the mixture was stirred for 1.5 hours and adjusted to a pH of 2 to 3 with 5N hydrochloric acid followed by extraction with three times with 400 ml of ethyl acetate. The extract was then back extracted with a 2% aqueous sodium bicarbonate solution and the resulting aqueous extract was rendered weakly acidic with 5N hydrochloric acid followed by extraction with 1.5 l of ethyl acetate. The ethyl acetate extract thus obtained was dried over anhydrous sodium sulfate and evaporated to dryness to obtain 570 mg of crude 7-(5-etoxycarbonamido-5-carboxyvaleramido)-3-(α-methoxy-p-ethoxycarbonyloxycinnamoyloxymethyl)-7-methoxy-3-cephem-4-carboxylic acid. The compound thus obtained was then dissolved in 4 ml of methanol, and the solution was passed through a column of Sephadex LH-20 (a product of Pharmacia Fine Chemicals) (75 ml), and the column was developed with methanol. The effluents which were found to contain the desired product of this invention were combined and the solvent was evaporated to obtain 360 mg of 7-(5-ethoxycarboamido-5-carboxyvaleramido)-3-(α-methoxy-p-ethoxycarbonyloxycinnamoyloxymethyl)-7-methoxy-3-cephem-4-carboxylic acid.

EXAMPLE 3

0.59 g of 7-(5-carboxyvaleramido)-3-(α-methoxy-p-hydroxycinnamoyloxymethyl)-7-methoxy-3-cephem-4-carboxylic acid was dissolved in 100 ml of water and 20 ml of acetone was added to the solution. A solution of 0.55 g of propionyl chloride dissolved in 20 ml of acetone was then added dropwise to the mixture while maintaining the reaction mixture at a pH of 7.5 to 8.0 by addition of 1N sodium hydroxide. After completion of addition, the resulting reaction mixture was stirred at room temperature for 2 hours and adjusted to a pH of 5.0. Acetone was removed from the reaction mixture under reduced pressure, and the mixture was adjusted to a pH of 3 with 1N hydrochloric acid and extracted with 200 ml of ethyl acetate. The ethyl acetate extract was back extracted with a 2% aqueous sodium bicarbonate solution and extracted at a pH of 3 again with ethyl acetate. The extract thus obtained was then dried over anhydrous sodium sulfate to obtain 0.6 g of crude 7-(5-propionylamido-5-carboxyvaleramido)-3-(α-methyoxy-p-propionyloxycinnamoyloxymethyl)-7-methoxy-3-cephem-4-carboxylic acid.

Melting Point: 130°–135° C (with decomposition)
Elemental Analysis:
Calcd. for $C_{33}H_{41}N_3O_{15}S$ (%): C, 52.8; H, 5.5; N, 5.6; S, 4.1. Found (%): C, 53.1; H, 5.7; N, 5.1; S, 4.0.

EXAMPLE 4

0.59 g of 7-(5-amino-5-carboxyvaleramido)-3-(α-methoxy-p-hydroxycinnamoyloxymethyl)-7-methoxy-3-cephem-4-carboxylic acid was dissolved in 100 ml of water and 50 ml of acetone was added to the solution. 3.5 ml of a 30% solution of carbobenzyloxy chloride dissolved in toluene was then added to the mixture and the reaction mixture was stirred vigorously for 3 hours while maintaining the reaction mixture at a pH of 7.5 to 8.0. After completion of the reaction, toluene and acetone were removed substantially completely, the residue was worked up in the same manner as described in Example 3 to obtain 0.65 g of 7-(5-benzyloxycarboamido-5-carboxyvaleramido)-3-(α-methoxy-p-benzyloxycarbonyloxycinnamoyloxymethyl-7-methoxy-3-cephem-4-carboxylic acid.

Melting Point: 155°–160° C (with decomposition)
Elemental Analysis: Calcd. for $C_{41}H_{41}N_3O_{15}S$ (%): C, 58.2; H, 4.85; N, 5.0; S, 3.7. Found (%); C, 58.4; H, 4.9; N, 4.5; S, 3.5.

EXAMPLE 5

*Streptomyces viridochromogenes* SF-1584 strain was cultured under an aerobic condition in a culture medium containing 1.5% glycerin, 1.5% dextrin, 2.0% soybean meal and 0.15% calcium carbonate at a pH of 7 and a temperature of 28° C for 65 hours. One liter of the filtrate which is free from mycelium obtained by the above cultivation was passed through a column (100 ml) of Diaion HP-20 (a product of Mitsubishi Chemical Industries Ltd., Japan) and the column was washed with water and eluted gradiently with aqueous methanol solutions having concentrations of 20 to 60% by volume. The fractions containing the desired compound of the formula (II) which were predominantly eluted with a 40% aqueous methanol solution (the total volume: 150 ml) were combined and concentrated. The concentrate thus obtained was cooled to 5° C, and a solution of 3.0 g of ethoxycarbonyl chloride dissolved in 5 ml of acetone was added dropwise thereto while maintaining the mixture at a pH of 7.5 to 8 with addition of an aqueous solution of sodium bicarbonate. After completion of the addition, the mixture was stirred for further 3 hours. The resulting reaction mixture which showed a negative reaction with ninhydrin was adjusted to a pH of 3.5 with 1N HCl and extracted with two 50 ml portions of ethyl acetate. The combined ethyl acetate extracts were back extracted with 50 ml of an aqueous sodium bicarbonate (pH 7.5) and again adjusted to a pH of 3.0 with 1N HCl, followed by extraction with two 20 ml portions of ethyl acetate. The combined extracts were then dehydrated over anhydrous sodium sulfate and dried to obtain 210 mg of crude 7-(5-ethoxycarboamide-5-carboxyvaleramido)-3-(α-methoxy-p-ethoxycarbonyloxycinnamoyloxymethyl)-7-methoxy-3-cephem-4-carboxylic acid.

While the invention has been described with reference to specific embodiments thereof, it will be apparent to one skilled in the art that various modifications and changes can be made therein without departing from the spirit and scope thereof.

What is claimed is:

1. A process for isolating a 7-(5-acylamido-5-carboxyvaleramido)-3-(α-methoxy-p-acyloxycinnamoyloxymethyl)-7-methoxy-3-cephem-4-carboxylic acid represented by the formula

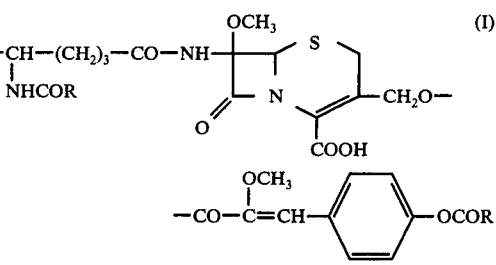

wherein R represents alkoxy group having 1 to 4 carbon atoms which may be substituted with halogen atoms; or an arylalkoxy group having 1 to 4 carbon atoms in the alkoxy moiety; the aryl moiety being optionally substituted with halogen atoms, and the salt thereof, from a fermentation broth which comprises cultivating streptomyces viridochromogenes SF-1584 strain which is capable of producing 7-(5-amino-5-carboxyvaleramido)-3-(α-methoxy-p-hydroxycinnamoyloxymethyl)-7-methoxy-3-cephem-4-caboxylic acid of the formula (II)

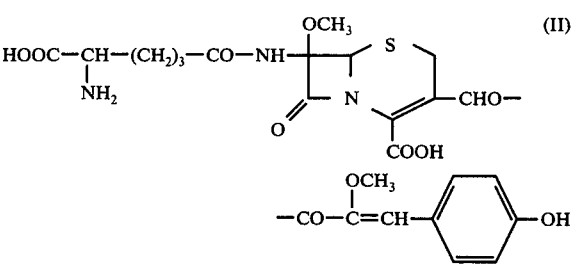

in a culture medium, adding an acylating agent of the formula (III)

RCOX            (III)

wherein R is as defined above and X represents a halogen atom, in a molar ratio of 2 to 40 moles of said acylating agent per mole of the compound of the formula (II) at a temperature below about 50° C at a pH of from about 7.5 to 8.0 and separating the thus obtained acylate of the formula (I) from said fermentation broth by precipitating and/or extracting with a solvent.

2. A process of claim 1, wherein said separation step is carried out by precipitation of the compound of formula (I) in said fermentation broth and recovery thereof.

3. The process of claim 1, wherein said separation is carried out by solvent extraction of the compound of formula (I) from said fermentation broth.

* * * * *